United States Patent [19]
Martinson et al.

[11] Patent Number: 5,569,462
[45] Date of Patent: Oct. 29, 1996

[54] METHODS FOR ENHANCING VASCULARIZATION OF IMPLANT DEVICES

[75] Inventors: Laura A. Martinson; James H. Brauker, both of Lake Villa; Robert C. Johnson, Bartlett; Thomas Loudovaris, Grayslake, all of Ill.

[73] Assignee: Baxter International Inc., Deerfield, Ill.

[21] Appl. No.: 414,061

[22] Filed: Mar. 31, 1995

Related U.S. Application Data

[62] Division of Ser. No. 126,540, Sep. 24, 1993, abandoned.

[51] Int. Cl.$^6$ .............................. A61F 2/02; A61K 9/22; C12N 5/02
[52] U.S. Cl. .................. 424/424; 424/423; 435/240.22; 514/964; 604/890.1; 604/892.1; 623/11
[58] Field of Search ..................................... 424/423, 424, 424/426; 435/240.22; 514/964; 604/890.1, 892.1; 623/11

[56] References Cited

U.S. PATENT DOCUMENTS

| | | | |
|---|---|---|---|
| 3,093,831 | 6/1963 | Jordan | 623/12 |
| 3,313,289 | 4/1967 | Kapral | 604/93 |
| 3,646,616 | 3/1972 | Keshin | 623/12 |
| 3,699,956 | 10/1972 | Kitrilakis et al. | 604/175 |
| 3,967,618 | 7/1976 | Zaffaroni | 128/833 |
| 3,993,072 | 11/1976 | Zaffaroni | 424/430 |
| 4,011,861 | 3/1977 | Enger | 607/121 |
| 4,069,307 | 1/1978 | Higuchi et al. | 424/432 |
| 4,180,560 | 12/1979 | Katz et al. | 424/426 |
| 4,192,308 | 3/1980 | Michaels | 604/892.1 |
| 4,207,390 | 6/1980 | Oehrlein et al. | 429/179 |
| 4,217,664 | 8/1980 | Faso | 606/108 |
| 4,266,999 | 5/1981 | Baier | 156/227 |
| 4,298,002 | 11/1981 | Ronel et al. | 424/424 |
| 4,306,318 | 12/1981 | Mano et al. | 623/1 |
| 4,309,776 | 1/1982 | Berguer | 3/1 |

(List continued on next page.)

FOREIGN PATENT DOCUMENTS

| | | |
|---|---|---|
| 1196862 | 11/1985 | Canada. |
| 0127989 | 12/1984 | European Pat. Off.. |
| 0188309 | 7/1986 | European Pat. Off.. |
| 0213908A2 | 3/1987 | European Pat. Off.. |
| 0213908 | 3/1987 | European Pat. Off.. |
| 0232543 | 8/1987 | European Pat. Off.. |
| 0259536 | 3/1988 | European Pat. Off.. |
| 0277678 | 8/1988 | European Pat. Off.. |
| 0359575 | 3/1990 | European Pat. Off.. |
| 0359575A2 | 3/1990 | European Pat. Off.. |
| 0370292 | 5/1990 | European Pat. Off.. |

(List continued on next page.)

OTHER PUBLICATIONS

Anderson, James M.: "Inflammatory Response to Implants," *Trans. Am. Soc. Artif. Intern. Organs*, vol. XXXIV, 1988, pp. 101–107.

Campbell, Craig E. and von Recum, Andreas F.: "Microtopography and Soft Tissue Response," *Journal of Investigative Surgery*, vol. 2, 1989, pp. 51–74.

Christenson, L. et al.: "Tissue Reaction to Intraperitoneal Polymer Implants: Species Difference and Effects of Corticaid and Doxorubicin," *Journal of Biomedical Materials Research*, vol. 23, 1989, pp. 705–718.

(List continued on next page.)

Primary Examiner—Carlos Azpuru
Attorney, Agent, or Firm—Banner & Allegretti, Ltd.

[57] ABSTRACT

Methods for enhancing vascular support of cells housed within an implanted apparatus are disclosed. The methods comprise placing a population of therapeutic substance-producing cells into the cell receiving chamber of an immunoisolation apparatus, implanting the apparatus into a patient, and administering an immunomodulatory agent to the patient. The immunomodulatory agent increases the number of close vascular structures in the vicinity of the implanted device, which increases the long term survival of the cell population housed therein.

14 Claims, 3 Drawing Sheets

U.S. PATENT DOCUMENTS

| | | | |
|---|---|---|---|
| 4,309,996 | 1/1982 | Theeuwes | 424/424 |
| 4,352,883 | 10/1982 | Lim | 435/178 |
| 4,352,888 | 10/1982 | Sefton | 435/290.1 |
| 4,353,888 | 10/1982 | Sefton | 424/25 |
| 4,368,737 | 1/1983 | Ash | 604/175 |
| 4,374,669 | 2/1983 | MacGregor | 419/9 |
| 4,378,016 | 3/1983 | Loeb | 424/424 |
| 4,391,909 | 7/1983 | Lim | 435/1.1 |
| 4,413,359 | 11/1983 | Akiyama et al. | 623/11 |
| 4,475,916 | 10/1984 | Hinnelstein | 424/424 |
| 4,505,277 | 3/1985 | Klesius et al. | 128/769 |
| 4,508,113 | 4/1985 | Malaney | 128/849 |
| 4,542,539 | 9/1985 | Rowe, Jr. et al. | 623/16 |
| 4,553,272 | 11/1985 | Mears | 623/1 |
| 4,557,724 | 12/1985 | Gregonis et al. | 604/49 |
| 4,576,608 | 3/1986 | Homsy | 623/11 |
| 4,597,765 | 7/1986 | Klatt | 623/11 |
| 4,601,893 | 7/1986 | Cardinal | 424/424 |
| 4,624,847 | 11/1986 | Ayer et al. | 424/467 |
| 4,657,544 | 4/1987 | Pinchuk | 623/1 |
| 4,664,669 | 5/1987 | Ohyabu et al. | 623/66 |
| 4,670,286 | 6/1987 | Nyilas et al. | 427/2.24 |
| 4,673,566 | 6/1987 | Goosen et al. | 424/424 |
| 4,681,582 | 7/1987 | Yamamoto | 424/450 |
| 4,684,524 | 8/1987 | Eckenhoff et al. | 424/469 |
| 4,685,447 | 8/1987 | Iversen et al. | 128/899 |
| 4,686,098 | 8/1987 | Kopchick et al. | 424/424 |
| 4,687,481 | 8/1987 | Nuwayser | 424/449 |
| 4,689,293 | 8/1987 | Goosen et al. | 435/182 |
| 4,712,553 | 12/1987 | MacGregor | 606/231 |
| 4,723,947 | 2/1988 | Konopka | 604/272 |
| 4,743,252 | 5/1988 | Martin, Jr. et al. | 623/1 |
| 4,795,459 | 1/1989 | Jauregui | 623/1 |
| 4,798,585 | 1/1989 | Inoue et al. | 604/93 |
| 4,803,168 | 2/1989 | Jarvis, Jr. | 435/240.22 |
| 4,804,381 | 2/1989 | Turina et al. | 623/1 |
| 4,806,355 | 2/1989 | Goosen et al. | 424/424 |
| 4,816,339 | 3/1989 | Tu et al. | 428/421 |
| 4,826,480 | 5/1989 | Diaz et al. | 604/49 |
| 4,855,141 | 8/1989 | Eckenhoff et al. | 424/423 |
| 4,871,366 | 10/1989 | von Recum et al. | 623/11 |
| 4,871,542 | 10/1989 | Vilhardt | 424/423 |
| 4,877,029 | 10/1989 | Valentini et al. | 606/152 |
| 4,878,895 | 11/1989 | Klesius et al. | 604/49 |
| 4,878,913 | 11/1989 | Aebischer et al. | 623/12 |
| 4,880,006 | 11/1989 | Albrektsson et al. | 128/630 |
| 4,892,538 | 1/1990 | Aebischer et al. | 604/891.1 |
| 4,911,717 | 3/1990 | Gaskill, III | 604/891.1 |
| 4,922,926 | 5/1990 | Hirschberg et al. | 607/120 |
| 4,936,317 | 6/1990 | MacGregor | 607/120 |
| 4,937,196 | 6/1990 | Wrasidlo | 435/297.2 |
| 4,950,483 | 8/1990 | Ksander et al. | 424/422 |
| 4,990,138 | 2/1991 | Bacich et al. | 604/96 |
| 5,002,661 | 3/1991 | Chick et al. | 210/192 |
| 5,011,472 | 4/1991 | Aebischer et al. | 604/50 |
| 5,015,476 | 5/1991 | Cochrum et al. | 424/423 |
| 5,024,670 | 6/1991 | Smith et al. | 623/18 |
| 5,077,215 | 12/1991 | McAuslan et al. | 435/240.23 |
| 5,100,392 | 3/1992 | Orth et al. | 604/175 |
| 5,112,614 | 5/1992 | Magruder et al. | 424/422 |
| 5,156,623 | 10/1992 | Hakamatsuka et al. | 623/11 |
| 5,201,728 | 4/1993 | Giampapa | 604/891.1 |
| 5,213,574 | 5/1993 | Tucker | 604/93 |
| 5,219,361 | 6/1993 | von Recum et al. | 623/11 |
| 5,262,055 | 11/1993 | Bae et al. | 210/645 |
| 5,324,518 | 6/1994 | Orth et al. | 424/423 |
| 5,326,568 | 7/1994 | Giampapa | 424/426 |
| 5,344,454 | 9/1994 | Clarke et al. | 623/11 |

FOREIGN PATENT DOCUMENTS

| | | |
|---|---|---|
| 88 13 531 | 5/1989 | Germany . |
| 4006145A1 | 8/1990 | Germany . |
| 8078845 | 5/1988 | Japan . |
| 2185408 | 7/1987 | United Kingdom . |
| WO83/03536 | 10/1983 | WIPO . |
| WO84/01287 | 4/1984 | WIPO . |
| WO87/03091 | 11/1987 | WIPO . |
| WO88/03785 | 6/1988 | WIPO . |
| WO88/02526 | 7/1988 | WIPO . |
| WO88/03540 | 10/1988 | WIPO . |
| WO89/00742 | 2/1989 | WIPO . |
| WO89/03705 | 8/1989 | WIPO . |
| WO91/00119 | 1/1991 | WIPO . |
| WO91/07486 | 5/1991 | WIPO . |
| WO92/07575 | 5/1992 | WIPO . |
| WO92/07525 | 5/1992 | WIPO . |
| WO92/17130 | 10/1992 | WIPO . |

OTHER PUBLICATIONS

Colton et al.: "Bioengineering in Development of the Hybrid Artificial Pancreas," *Transactions of the ASME*, vol. 113, May 1991.

Klomp, Gregory F. et al.: "Macroporous Hydrogel Membranes for a Hybrid Artificial Pancreas," *Journal of Biomedical Materials Research*, vol. 17, 1983 pp. 865–871.

Knighton, David R. and Fiegel, Vance D.: "Macrophage-derived Growth Factors in Wound Healing," *Am. Rev. Respir. Dis.*, 140, 1989, pp. 1108–1111.

Knighton, David R. et al.: "Oxygen Tension Regulates the Expression of Angiogenesis Factor by Macrophages," *Science*, Sep., 1981.

Lanza, Robert P. "Islet Transplantation With Immunoisolation" in *Diabetes*, vol. 41, Dec. 1992, pp. 1503–1510.

Menger, M. D. et al. "The Influence of Cyclosporine on the Microvasculature of Xenogeic Pancreatic Islet Grafts" in *Transplantation Proceedings*, vol. 23, Aug. 1991, pp. 2217–2218.

Miller, K. M. et al.: "Characterization of Biomedical Polymer Adherent Machrophages: Interleukin 1 Generation and Scanning Electron Microscopy Studies," *Biomaterials*, vol. 10, Apr. 1989, pp. 187–196.

Polverini et al.: "Activated Macrophages Induce Vascular Proliferation," *Nature*, vol. 269, Oct. 27, 1977, pp. 804–806.

Rooth, Pal et al. "Prevention of Detrimental Effect of Cyclosporin A on Vascular Ingrowth of Transplanted Pancreatic Islets With Verapamil" in *Diabetes*, vol. 38, Suppl. 1, Jan. 1989, pp. 202–205.

Scharp, David W. et al.: "Islet Immuno–Isolation: The Use of Hybrid Artificial Organs to Prevent Islet Tissue Rejection",: *World Journal of Surgery*, 1984, pp. 221–229.

Schmidt, J. A. and von Recum, A. F.: "Texturing of Polymer Surfaces at the Cellular Level," *Biomaterials*, vol. 12, 1991, pp. 385–389.

Woodward, Stephen C. and Salthouse, Thomas N.: "The Tissue Response to Implants and Its Evaluation by Light Microscopy," *Handbook of Biomaterials Evaluation*, pp. 364–378.

Rooth et al. (1989), "Prevention of Detrimental Effect of Cyclosporin A on Vascular Ingrowth of Transplanted Pancreatic Islets With Verapamil," *Diabetes*, vol. 38, pp. 202–205.

Menger et al. (1991), "The Influence of Cyclosporine on the Microvasculature of Xenogenic Pancreatic Islet Grafts," *Transplantation Proceedings*, vol. 23, 2217–2218.

Lanza, Robert P. (1992), "Islet Transplantation With Immunoisolation," *Diabetes*, vol. 41, pp. 1503–1510.

Langer and Vacanti (1993), "Tissue Engineering," *Science*, vol. 260, pp. 920–925.

Anderson, W. (1992), "Human Gene Therapy," *Science*, vol. 256, pp. 808–813.

Anderson, J. (1988), "Inflammatory Response to Implants," *J. Trans. Am. Soc. Artif. Intern. Organs*, vol 34, pp. 101–107.

Carotenuto et al. (1992), European Assoc. Study Diabetes, 28th Annual Meeting, Abstract 730.

Schreiber and Crabtree (1992), "The Mechanism of Action of Cyclosporin A and FK506," *Immunol. Today*, vol. 13, pp. 136–142.

Golumbek et al. (1991), "Treatment of Established Renal Cancer by Tumor Cells Engineered to Secrete Interleukin-4," *Science*, vol 254, pp. 713–716.

Townsend and Alison (1993), "Tumor Rejection After Direct Costimulation of $CD8^{30}$ T Cells by B7-Transfected Melanoma Cells," *Science*, vol. 259, pp. 368–370.

Trojan et al. (1993), "Treatment and Prevention of Rat Glioblastoma by Immunogenic C6 Cells Expressing Antisense Insulin–Like Growth Factor I RNA," *Science*, vol. 259, pp. 94–97.

Scharp et al. (1984), "Islet Immuno–isolation: The Use of Hybrid Artificial Organs to Prevent Islet Tissue Rejection," *World J. Surg.*, vol. 8, pp. 221–229.

METHODS FOR ENHANCING VASCULARIZATION OF IMPLANT DEVICES

This is a division of application Ser. No. 08/126,540, filed on Sep. 24, 1993, now abandoned.

FIELD OF THE INVENTION

This invention relates to methods for enhancing vascular support of cells housed within an implanted apparatus. In particular, this invention relates to the use of immunomodulatory agents to increase the number of close vascular structures in the vicinity of the implanted apparatus.

BACKGROUND OF THE INVENTION

It has long been recognized that certain diseases potentially could be therapeutically treated by transferring cells, tissues, or organs into a patient having the particular disease. Attempts to carry out such transfers have been ongoing for many years, and have met with some success. However, transferred cells, tissues, or organs are often rejected by the patient's immune system.

Devices carrying cells within or on a polymeric matrix have been suggested to be useful for obtaining successful implantation of cells into a patient. Lanza, R. et al., Diabetes 41:1503 (1992); Langer, R. and Vacanti, J. Science 260:920 (1993). As used herein, implantation refers to the grafting or insertion of an object, with or without cells, into the body of a patient. Transplantation refers to the transfer of unenclosed tissues or organs, without additional objects such as supports or enclosures, into the body of a patient. The polymeric matrix may be composed of a naturally occurring substance such as alginate or collagen. Alternatively, the matrix may be composed of a synthetic polymer such as acrylonitrile-vinyl chloride copolymer or polyacrylates. Several types of devices have been disclosed, including extravascular compartments, macrocapsules, and microcapsules. The devices generally have membranes permeable to low molecular weight molecules and proteins, but not permeable to cells, high molecular weight molecules, or subcellular complexes.

In recent years, gene transfer into cells has been proposed as a useful technique for treatment of certain diseases and medical conditions. The transfer of extrinsic genetic material into cells is often referred to as transduction, transfection, or genetic engineering, and the employment of such cells to treat disease in vivo is often referred to as gene therapy. Various gene therapy methods have been proposed or are in testing. Anderson, W., Science 256:208 (1992).

Difficulties have been noted, however, in transplantation and implantation of cells, whether or not genetically engineered. Conventional implant devices and methodologies usually fail to keep the implanted cells alive for a time sufficient to provide the intended therapeutic benefit. For a period of time after implantation, the tissues in the vicinity of the implanted device can be characterized as ischemic. That is, the local vasculature is inadequate to ensure a sufficient flow of blood to the tissues in the region closely surrounding the implanted device. Conventional devices generally induce a fibrous capsule composed of layers of fibroblasts, collagen, macrophages, foreign body giant cells and small lymphocytes. The fibrous capsule has been thought to cause ischemic necrosis and thereby to reduce or inhibit the flux of nutrients, cellular waste products and therapeutic substances between the device and the patient. Lanza, R. et al., supra; Langer, R. and Vacanti, J., supra.

The body's response to implantation of a device involves several phases. An acute-phase inflammatory reaction is initiated following activation of tissue macrophages and release of the cytokines TNF-$\alpha$, interleukin-1 and interleukin-6. The result is a fever response, increased vascularization, and an influx of macrophages and lymphocytes to the site of implantation. The recruited macrophages may release factors that are damaging to implanted cells. In humans, the acute phase of inflammation usually lasts for 2–3 days during which the wound becomes sealed by a fibrin clot within which polymorphonuclear leukocytes act to prevent invasion of microorganisms.

The predominant bioactive cells in the inflammatory process are mononuclear cells. Mononuclear cells can differentiate as macrophages and become actively phagocytic. Macrophages in fact play a pivotal role in the response of tissue to implants. Anderson, J. Trans. Am. Soc. Artif. Intern. Organs 34:101 (1988). Some mononuclear cells coalesce and differentiate as multinucleated giant cells, which are also phagocytic. The phagocytic mononuclear cells dispose of those cellular and tissue components that are not readily solubilized by enzymes released by granulocytes or activated by local circulatory factors. This phagocytic process generally characterizes the terminal phase of the acute inflammatory reaction. However, continued presence of foreign materials can cause persistence of this inflammatory reaction, recognized as chronic inflammation. Mononuclear cells and their differentiated progeny may be referred to as inflammatory cells.

The response to implantation of a device containing cells or other antigenic materials also involves immune system recognition, which is apparent about 10 to 14 days after implantation in mammals. The severity of the immune response generally is determined by the immunogenicity of the implanted cells. Isogeneic cells or allogeneic cells generally lead to a low to moderate immune response and the host tissue immediately adjacent to the device being vascularized. However, xenogeneic cells generally induce a much more severe host cellular response, consisting of an extensive accumulation of inflammatory cells such as lymphocytes and macrophages. The halo of local inflammation around implanted devices housing xenogeneic cells is largely avascular.

Attempts have been made to inhibit the inflammatory response and to inhibit immune recognition and rejection of transplanted or implanted cells by supplying an agent such as cyclosporine A. A seeming disadvantage in use of cyclosporine A is that it is reported to inhibit neovascularization, which is important for successful implantation. In fact, cyclosporine A has been reported to interfere with establishment of isogeneic pancreatic transplants by inhibiting neovascularization. Carotenuto, P., et al., European Assoc. Study Diabetes, 28th Ann. Meeting, Abs. 730 (1992); Rooth, P. et al., Diabetes 38 (Suppl. 1): 202–5 (1989).

Thus, there is a continuing need for devices and methods that enhance neovascularization of implants so as to increase the rate of successful implantation and to increase the long term viability of implanted isogeneic, allogeneic and xenogeneic cells.

SUMMARY OF THE INVENTION

The present inventors have discovered a method for implanting viable cells in a patient. The cells may be selected to provide a clinical benefit to the patient. For example, the cells may provide a therapeutic substance that has clinical efficacy for a patient. A population of the viable cells is placed in an immunoisolation apparatus having structure defining a cell receiving chamber within the immunoisolation apparatus. The cell receiving chamber houses the viable cells to be implanted. The immunoisolation apparatus includes an immunoisolation zone that immunoisolates the cell receiving chamber from the patient's tissue environment in which the apparatus is implanted. After implantation in the patient, an immunomodulatory agent is administered to the patient in an amount and for a time effective to enhance vascularization of the implanted apparatus. The cell population may be placed in the cell receiving chamber of the apparatus either before or after implantation in the patient.

The viable cells may comprise cells that are xenogeneic, allogeneic and/or isogeneic to the patient in which the immunisolation apparatus is implanted. In addition, the viable cells may be genetically engineered to include an extrinsic nucleic acid construct that confers upon the cells the capability of producing the therapeutic substance. The immunomodulatory agent that is administered to the patient may be an antiinflammatory agent or an immunosuppressive agent. For example, an effective immunomodulatory agent of the present invention is cyclosporine A.

The immunoisolation apparatus may further comprise means for effecting close vascularization of the apparatus. The means for effecting close vascularization may comprise an outer surface of the apparatus whose composition and configuration is known to promote close vascularization of the apparatus following implantation. Such an outer surface of the apparatus is termed a vascularization zone. Alternatively, the means for effecting close vascularization may comprise one or more cells, termed vascularization cells, housed within the cell receiving chamber, wherein the cells produce an effective amount of a vascularizing substance that facilitates close vascularization of the apparatus. In a further embodiment, the apparatus can include both a vascularization zone as well as vascularizing cells. Generally, the immunoisolation zone of the apparatus is interposed between the vascularization zone and the cell receiving chamber.

The invention further includes a non-human mammal implanted with a device producing a therapeutic substance. The device comprises an immunoisolation apparatus having structure defining a cell receiving chamber within the apparatus, an immunoisolation zone that immunoisolates the cell receiving chamber, and a population of cells housed within the cell receiving chamber. The population of cells is capable of producing a therapeutic substance. The claimed non-human mammal further has been administered an immunomodulatory agent in an amount and for a time effective to enhance vascularization of the implanted device.

The invention also includes an article of manufacture comprising packaging material and an immunoisolation apparatus within the packaging material. The immunoisolation apparatus has structure defining a cell receiving chamber within the immunoisolation apparatus. The cell receiving chamber is designed to house viable cells to be implanted in a patient. The immunoisolation apparatus further includes an immunoisolation zone that immunoisolates the cell receiving chamber from the patient's tissue environment in which the apparatus is implanted. The packaging material further comprises a label indicating that the immunoisolation apparatus is for implantation into a patient and further indicating that the patient may be administered an immunomodulatory agent for enhancing vascularization of the implanted device.

DETAILED DESCRIPTION OF THE INVENTION

Figure 1:
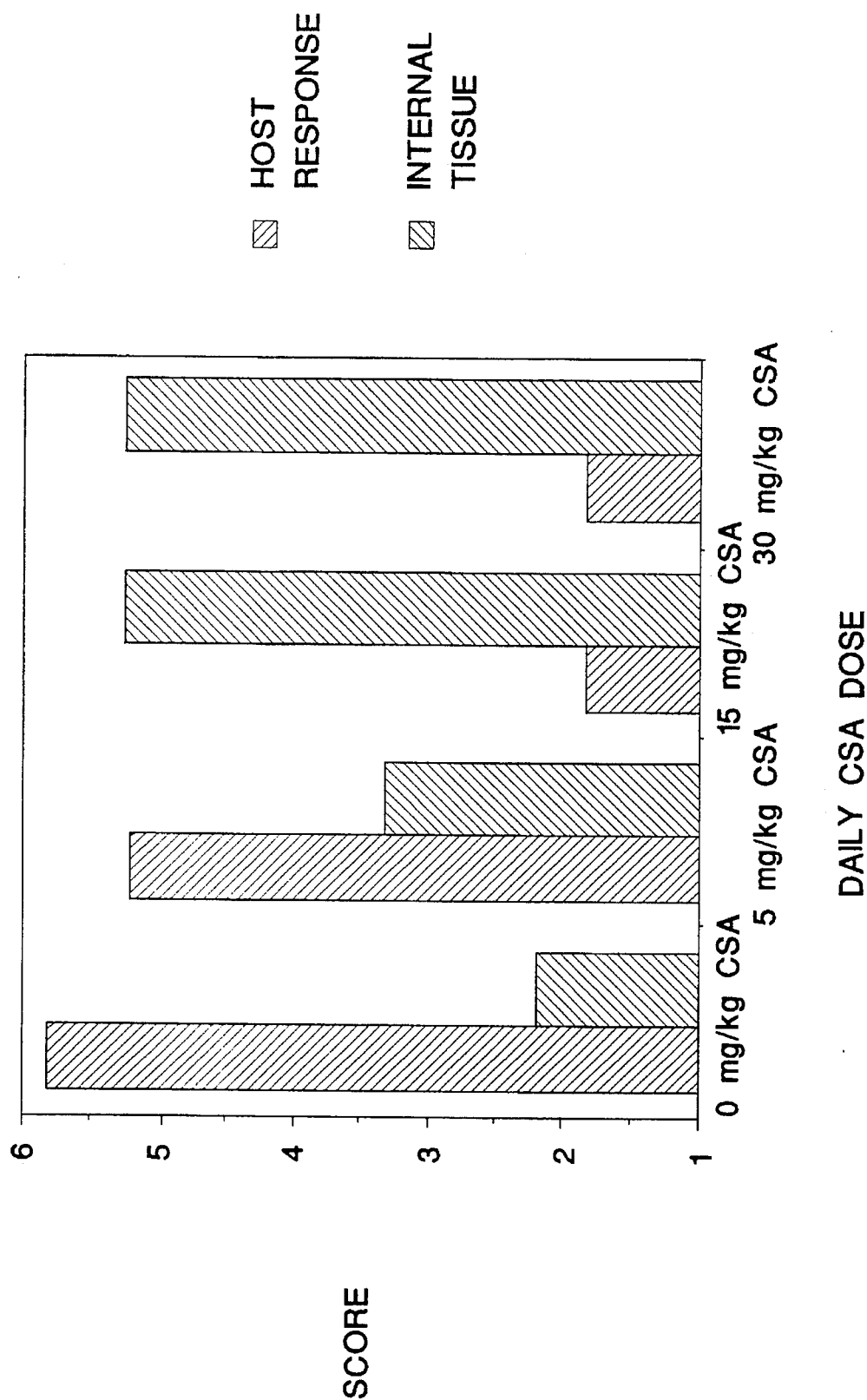
FIG. 1 is a bar graph showing the mean host response scores and the mean tissue survival scores for xenografts in rats after administration of cyclosporine A for three weeks.

A device for producing a therapeutic substance, comprising an implantable apparatus and cells housed therein, may be implanted in a patient and engenders an inflammatory response coincident to a period of ischemia. As used herein, a patient may be any animal, but is preferably a mammal, and is more preferably a human. The inventors previously have discovered that an inadequate flux of nutrients and waste products between the device and the patient's tissue during the ischemic period threatens the survival of the implanted cells. The present invention establishes for the first time that an immunomodulatory agent supplied to an implantation site does not inhibit neovascularization of a gene therapy device, but actually increases neovascularization.

The actual mechanism by which an immunomodulatory agent influences neovascularization of an implanted device is not understood. However, the inventors have discovered, as described in U.S. patent application Ser. Nos. 7/735,401 and 7/861,512, incorporated in their entirety by reference herein, that cell populations of a device may die during the ischemic period because the rate of nutrient influx and the rate of cellular waste product efflux are not sufficient to maintain cell viability. The viability of the cells is most threatened during the ischemic period.

During the ischemic period, an exudate forms a fluid barrier between the vascular system of a patient and an implanted apparatus. This barrier hinders the flux of nutrients and waste products between the patient's vascular system and the apparatus. The patient's inflammatory cells that enter the exudate region can function to create a metabolic sink. Such cells compete with cells of the device for the patient's extracellular nutrients and may extract these nutrients before they can be taken up by cells of the device. However, concentrations of nutrients present outside the device, although significantly reduced by the exudate barrier and metabolic sink effects, nevertheless are sufficient to sustain the implanted cells provided that neovascularization of the device is timely established. This is true even in the presence of a foreign body capsule.

The ischemic period ends when sufficient numbers of close vascular structures have formed within the exudate region close to the apparatus. Close vascularization comprises the formation of capillaries by the patient's tissues in the vicinity of the apparatus. Close vascular structures generally lie within about one cell layer of the surface of the apparatus, and usually within about 15 microns of the surface. The formation of new capillaries is often termed neovascularization. It is desirable to effect close vascularization of an implanted apparatus, because close vascular structures shorten the extracellular path that nutrients must travel to reach the apparatus, decrease the number of cells functioning as metabolic sinks between the vasculature and the apparatus, and therefore provide nutrients in higher concentrations to the implanted cells. Close vascularization also facilitates the transport of therapeutic substances generated by implanted cells of the device.

An apparatus suitable for the present invention is structured to have an interior chamber suitable for receiving and housing cells of the device. A suitable apparatus provides an immunoisolation zone, for example a first membrane, that prevents T cells, macrophages, and other immune system cells from entering the interior chamber of the apparatus. Such an apparatus is sometimes termed an immunoisolation apparatus because there is no direct, physical contact between cells in the apparatus and cells of the patient's immune system.

The apparatus optionally is endowed with means for effecting close vascularization, which may be provided, for example, by a second membrane. Alternatively, cells of the device may themselves provide means for effecting close vascularization by producing a substance promoting vascularization of the apparatus. Such a vascularization substance may be an angiogenesis factor or any material that directly or indirectly enhances vascularization. As another alternative, a second membrane and the cells together may provide means for effecting close vascularization. Another apparatus suitable for the present invention may have a single membrane providing both an immunoisolation zone and dose vascularization means. Examples of apparatuses suitable for the present invention are disclosed in PCT application 91/07486 and U.S. patent application Ser. Nos. 7/735,401 and 7/861,512, incorporated in their entirety by reference herein.

In a preferred apparatus, the means for effecting close vascularization comprises a membrane of porous polytetrafluorethylene (PTFE) material having a thickness of about 15 microns and a pore size of about 5 microns. As used herein, "pore size" refers to the maximum pore size of the material. The practitioner determines pore size using conventional bubble point methodology, as described in Pharmaceutical Technology, May 1983, pp. 36–42. The close vascularization membrane has a backing of polyester about 120 microns thick. This material is made by W. L. Gore and Associates (Elkton, Md.) under the trade name Gore-Tex™. In a preferred apparatus, an immunoisolation zone comprises a membrane of porous PTFE membrane material having a thickness of about 30–35 microns and a pore size of about 0.35–0.40 microns. This material is commercially available from Millipore Corporation under the trade name Biopore™. In a preferred apparatus, an immunoisolation membrane is interposed between the interior chamber and a close vascularization membrane. Further details and other embodiments of apparatuses, including suitable membrane materials, are set forth in U.S. patent application Ser. Nos. 7/735,401 and 7/861,512.

Cells of the device may comprise any cell population that is capable of producing a therapeutic substance. Cells of the device may be of a single tissue type and may even represent a clonal population. The cells may be modified to have extrinsic DNA constructs capable of effecting production of a therapeutic substance. Such transduced cells may be the direct products of DNA transfer events, or may be progeny of primary transformants.

The device may contain a mixed population of cells, if desired. A mixed population may be useful, for example, if one cell type stimulates neovascularization of the device and a second cell type produces a therapeutic substance. In fact, certain cell types have been found to stimulate neovascularization when housed within an implanted apparatus, while other cell types do not perform this function. For example, lung tissue, pancreatic islets, adult pancreatic ducts, and certain cultured cell lines of fibroblasts, mammary glands, and smooth muscle cells induce or stimulate neovascularization, compared to control implants having no cells housed therein. See U.S. patent application Ser. No. 7/861,512, incorporated in its entirety by reference herein. Such cells may provide means for close vascularization when housed within an apparatus. On the other hand, primary skin fibroblasts and microvascular endothelial cells do not induce neovascularization when housed within an implanted apparatus.

The same cell type may perform both the function of therapeutic substance production and the function of effecting close vascularization. Pancreatic islet cells are such a cell type, since they stimulate neovascularization and also produce a therapeutic substance, insulin.

A therapeutic substance may be any molecule having a salutary effect upon a medical condition or useful for a diagnostic purpose in a patient. A therapeutic substance may be a low molecular weight compound such as dopamine for treatment of Parkinson's disease, or a macromolecule such as a polypeptide. Such polypeptides may include, for example, hormones, growth factors, or enzymes in specific biosynthetic pathways. Production of a therapeutic substance may be an intrinsic property of cells of the device, as with pancreatic islet cells producing insulin. Alternatively, production of a therapeutic substance may be conferred by an extrinsic nucleic acid construct.

As used herein, extrinsic DNA construct or extrinsic gene construct refers to a nucleic acid sequence originating outside a recipient cell and introduced into a recipient cell by a DNA delivery technique. A DNA or gene construct may be manufactured using recombinant DNA technology known in the art, or may be a nucleic acid fragment purified from a source material without further manipulation. The extrinsic gene may be entirely composed of homologous sequences, i.e., sequences cloned, isolated, or derived from the same species from which the recipient cells derive. Alternatively, all or a portion of the extrinsic gene may be composed of sequences from species other than the species from which the recipient cells derive, hereinafter termed heterologous sequences. The extrinsic gene construct may be natural in that none of the regulatory sequences and coding sequences that may be a part of the gene are substantially or intentionally altered, or the extrinsic gene construct may be chimeric in that sequence fragments from various sources are present in the final gene construct. Examples of extrinsic DNA constructs introduced into cells include constructs expressing cytokines, cell surface molecules, or antisense sequences. Golumbek, P., et al., Science 254:713 (1991); Townsend, S. and Alison, P., Science 259:368 (1993); Trojan, J., et al., Science 259:94 (1993).

A gene for a therapeutic substance refers to an intrinsic or extrinsic nucleic acid sequence that confers upon a cell the capability of producing a therapeutic substance. A nucleic acid sequence capable of produring a therapeutic substance may comprise a coding sequence for one or more polypeptides. If a therapeutic substance gene encodes a polypeptide, the gene may be a genomic sequence including introns and other features, may be derived from a cDNA sequence or may be derived from a chemically synthesized nucleic acid sequence. A therapeutic substance gene will be necessary for production of a therapeutic substance, but, in some cases, will not be sufficient. Many polypeptides of therapeutic importance are modified, e.g., by glycosylation. Many important therapeutic polypeptides are secreted, requiring cellular signal peptide processing machinery. If a therapeutic substance gene comprises such polypeptides, additional sequence information may be provided by the cell or may be engineered into the extrinsic DNA construct. Examples of therapeutic substance genes are sequences that confer upon a cell the capability of producing human factor IX, human factor VIII, insulin, and human growth hormone. A therapeutic substance gene may be placed under the regulation of regulatory elements to ensure effective production of the substance.

An immunomodulatory agent is any agent that decreases the number of inflammatory cells and other immune system cells in the vicinity of a device and thereby enhances neovascularization. A preferred immunomodulatory agent is cyclosporine A. Schreiber, S. and Crabtree, G., Immunol. Today 13:136 (1992). Cyclosporine A suppresses antigen-activated T lymphocytes, and is thought to block production of lymphokines, especially interleukin-2 (IL-2). The inhibition of IL-2 production reduces T helper ($T_H$) cell proliferation and reduces the activation of various effector populations involved in inflammatory responses, such as activated macrophages, cytotoxic T lymphocytes, and $T_{DTH}$ cells (CD4+ $T_H$ cells involved in delayed-type hypersensitivity reactions).

Other immunomodulatory agents may be suitable for practicing the invention. Corticosteroids such as prednisolone and prednisone are potent antiinflammatory agents suitable for the invention. Immunosuppressing agents such as, without limitation, mycophenolic acid (MPA) (Syntex Research, Palo Alto, Calif.), mycophenolate mofetil (RS-61443) (Syntex Research, Palo Alto, Calif.), rapamycin, 15-deoxyspergualin (Bristol-Myers Squibb, Wallingford, Conn.) and FK506 (Fujisawa Pharmaceutical Co., Deerfield, Ill.) are also suitable for practicing the invention.

Supplying an immunomodulatory agent to enhance neovascularization of an implanted device is suitable for devices housing isogeneic, allogeneic, and/or xenogeneic cell populations. The basis for increased survival rates of xenogeneic cells may be due to a beneficial effect of the immunomodulatory agent on the acute-phase inflammatory reaction as well as on the host's immunologic response to the encapsulated xenogeneic cells. Isogeneic and/or allogeneic cells are thought to benefit primarily from a decrease in the acute-phase inflammatory reaction that occurs in response to implantation. This reduction in the acute-phase inflammatory reaction and/or immune response may facilitate healthier cell populations within the device. In turn, such cell populations are thought to be more capable of engendering neovascularization than are cells that have been adversely affected by an acute-phase inflammatory reaction or by a host immune response. Although such tissue-driven vascularization is likely an important component of the vascular response, it is also possible that a direct and harmful effect of local immune cells on formation of close vascular structures is lessened by administration of an immunomodulatory agent.

In one embodiment of the present invention, cells producing a desired therapeutic substance are placed within a cell receiving chamber of a suitable apparatus. The device is implanted into a selected patient intraperitoneally, intramuscularly or subcutaneously, as desired. The implantation site may depend upon the nature of the particular medical condition to be treated, but in most conditions it is believed that the implantation site is not critical to the practice of the invention, provided that the site is capable of supporting vascularization. Preferred sites include, without limitation, intraperitoneal fat sites, the omentum, various subcutaneous sites and sites beneath the capsule of the kidney. Cells may be placed in the apparatus after implantation of the apparatus, if desired.

The number of cells housed within the interior chamber of an apparatus and the average rate of production per cell of a therapeutic substance must combine to produce an overall amount of therapeutic substance sufficient to improve the patient's medical condition. The amount of therapeutic substance necessary to effect clinically significant improvement in the medical condition of a patient will depend upon several factors. One factor will be the severity of the particular medical condition. Additional treatments, e.g., surgery, prescription drugs, and the like may be indicated by a medical practitioner; the use of such treatments may affect the amount of therapeutic substance necessary to produce clinically significant improvement. The desired amount of therapeutic substance may be determined by clinical measures suitable for the medical condition being treated. Such clinical measures will be known to those skilled in the art.

The immunomodulatory agent may be administered concurrently with, prior to, or after implantation of an apparatus. The agent may be administered systemically, for example by oral administration, or locally, for example by subcutaneous injection near the implantation site.

The dose and length of time that an immunomodulatory agent is administered to a patient depend upon several factors. The amount of immunomodulatory agent reaching the cells of the device must be sufficiently high to promote vascularization but not so high as to induce clinically intolerable side effects (e.g., complete immunosuppression). The immunomodulatory agent dosage and duration can vary with the species of the patient and with the species of cells housed within the device. There also will be differences among individuals in the effective dose of immunomodulatory agent. The effective dose and duration of application may be determined for each individual patient by clinical methods known in the art. Preferred dosages of cyclosporine A in rats are provided in the Examples below. Preferred dosages of cyclosporine A in humans include, for example, 10–18 mg/kg/day from one day prior to implantation to 14 days post-implantation, followed by a maintenance dose of 5–10 mg/kg/day for a period appropriate for the individual patient.

The invention will be further understood with reference to the following illustrative embodiments, which are purely exemplary, and should not be taken as limiting the true scope of the present invention as described in the claims.

EXAMPLE 1

General Procedures

The following Examples teach the effect of cyclosporine A upon survival of encapsulated xenogeneic and isogeneic cells in rats. Twenty four male Lewis rats (Harlan) were used in the experiments. All animals were maintained according to standard procedures for care and use of laboratory animals. Animals were divided into four groups of six animals, the groups differing in the daily dosage of cyclosporine A (CSA) as follows:

| | |
|---|---|
| Group I | 0 mg CSA/kg body weight |
| Group II | 5 mg CSA/kg body weight |
| Group III | 15 mg CSA/kg body weight |
| Group IV | 30 mg CSA/kg body weight. |

CSA was obtained from Sandoz Pharmaceuticals Corp. as a 100 mg/ml solution (Lot #670 S 7954). CSA was diluted with autoclaved, food grade olive oil (Fillippo Berio, Lot #026BG) to make stock solutions having 5, 15, and 30 mg/ml CSA. One ml of the appropriate amount of CSA stock solution per kg body weight was administered daily to each animal by oral gavage. CSA administration began one day prior to implantation of apparatuses, and continued for 21 days after implantation.

Isogeneic (Lewis rat) fetal lung tissue and xenogeneic (ICR mouse) fetal lung tissue were obtained as described, for example, at page 28 of U.S. patent application Ser. No. 7/861,512, incorporated herein by reference. The isogeneic and xenogeneic tissues were encapsulated separately in immunoisolation devices, with approximately 10 µl of minced lung tissue per device. The immunoisolation devices employed were "Bogg's chamber" devices, described in U.S. patent applications Ser. Nos. 7/735,401 and 7/861,512, incorporated herein by reference. Apparatuses were surgically implanted the same day as encapsulation of tissue in the device. Two apparatuses were surgically implanted into each rat, one apparatus into each of the two epididymal fat pads. One of the two apparatuses contained isogeneic cells and the other apparatus contained xenogeneic cells.

On the 22nd day after surgery, 3 animals from each group were sacrificed, and each apparatus was examined histologically as described below. The remaining 3 rats in each group were maintained in the laboratory without further CSA administration and were sacrificed on the 42nd day after surgery.

Each apparatus was removed, fixed in 2% glutaraldehyde, embedded in paraffin, sectioned, and stained with hematoxylin and eosin. Stained sections were examined by light microscopy and scored for host tissue response, survival of implanted cells, and vascularization. The scoring system used to evaluate the histological appearance of encapsulated cells and host tissue reaction is shown in Table 1. Under this system, a score of 6 is most desirable when the health status of the implanted cells is being scored, and a score of 1 is most desirable when the host tissue response is being scored.

TABLE 1

Scoring System for Histological Evaluation of Apparatuses

| | Histological Appearance of: | |
|---|---|---|
| Score | Implanted Cells | Host Tissue Response |
| 1 | No living tissue | Low level macrophage reaction |
| 2 | Scattered living cells, mostly dead cells | Intermediate macrophage reaction, or ordered fibroblasts |
| 3 | Less than 50% of cells alive | High macrophage reaction or standard foreign body response |
| 4 | More than 50% of cells alive | High macrophage reaction plus some lymphocytes |
| 5 | Living epithelial cells predominate | Heavy reaction, macrophage plus lymphocytes, plasma cells |
| 6 | Differentiated tissues | Extremely high reaction, macrophage plus lymphocytes, plasma cells |

Numbers of close vascular structures were determined as follows. Histological sections were taken through the diameters of the circular Boggs chamber devices and examined with light microscopy. Total numbers of close vascular structures on the external surfaces of the sectioned vascularizing membranes were enumerated. Close vascular structures were identified as blood vessels located within about 15 µm of the outer surface of the vascularizing membrane material and separated from the outer surface by no more than one cell, as well as blood vessels located within the vascularizing membrane material itself.

EXAMPLE 2

Effect of a 3 Week Cyclosporine A Treatment on Xenogeneic Apparatuses

Histological examination of xenografted cells and host tissue surrounding the xenografts showed that encapsulated xenogeneic cells from Group I (no CSA) animals were rejected by 21 days after implantation (Table 2). The xenografts were surrounded by a severe host inflammatory response, and the implanted xenogeneic lung tissue was destroyed. Xenografts from animals treated with 5 mg CSA/kg (Group II) were surround by a strong host immune response. Limited survival of fibroblasts and epithelial cells was observed microscopically in Group II xenogeneic cells.

As shown in Table 2, scores for xenogeneic cells were very good in animals treated with 15 mg CSA/kg (Group III) or 30 mg CSA/kg (Group IV), indicating that administration of CSA at these levels allowed survival of xenogeneic cells in the device. The tissue response of the host to the implanted apparatus was extremely mild in both groups. Compared to the host tissue reaction in Group I, the inflammatory response was dramatically reduced at these levels of CSA. The mean scores from Table 2 for xenogeneic cell survival and for host tissue response are graphically presented in FIG. 1.

Figure 2:
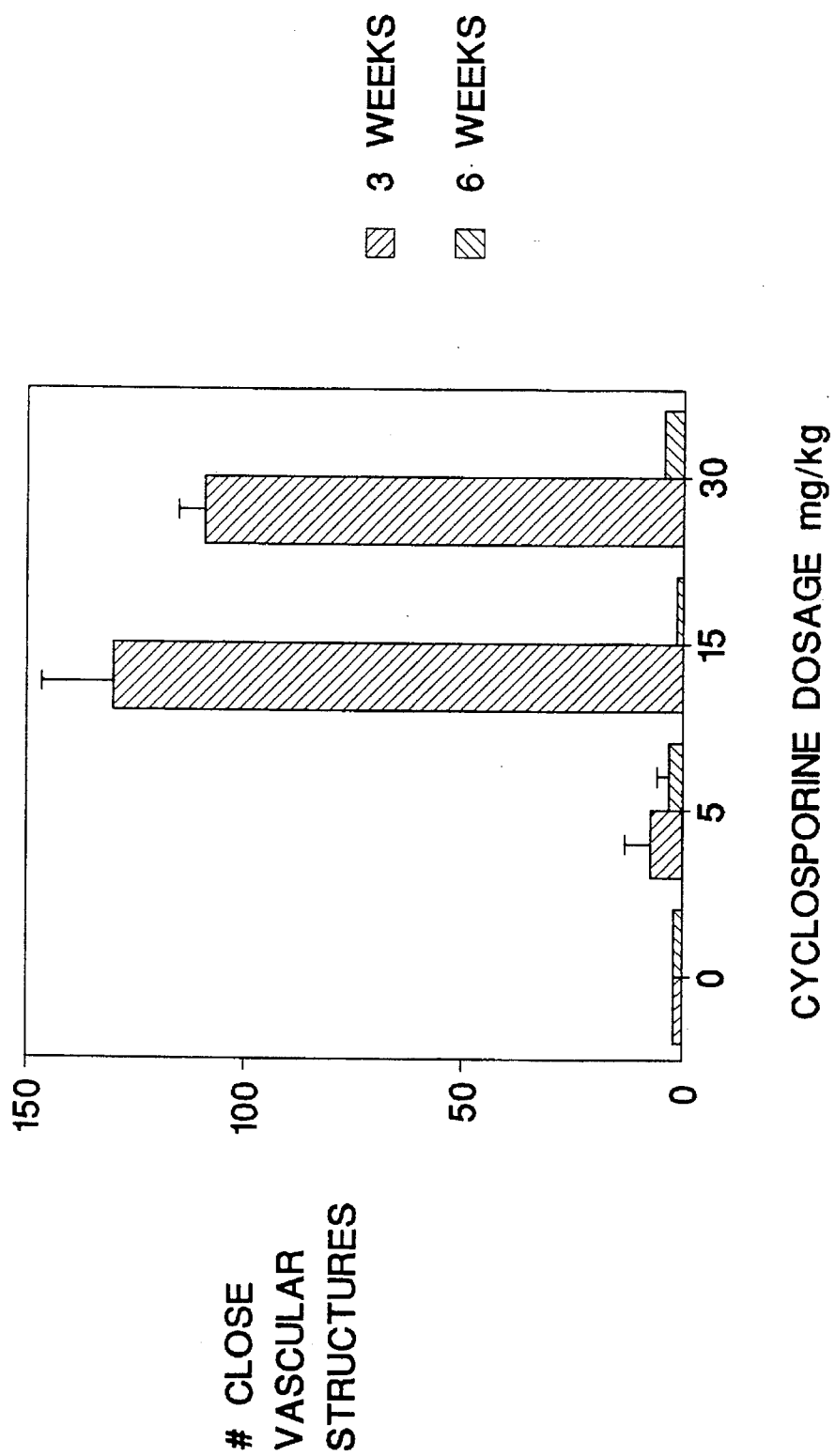
FIG. 2 is a bar graph comparing the mean number of close vascular structures for xenografts after daily administration of cyclosporine A for three weeks to the mean number for xenografts after daily administration of cyclosporine A for three weeks followed by no cyclosporine A for three weeks.

Xenografts appeared to be well vascularized after 3 weeks in the presence of 15 mg/kg or more of CSA, as shown by the number of close vascular structures. Xenografts at 15 and 30 mg CSA/kg had an average of 129 and 107 close vascular structures per apparatus, respectively (Table 2). The dramatic increase in the number of close vascular structures at 15 and 30 mg CSA/kg compared to 0 mg CSA/kg indicates that CSA is very effective at facilitating neovascularization of xenogeneic cells in an implanted device. The mean number of xenograft close vascular structures from Table 2 is shown graphically in FIG. 2 (stippled bars).

TABLE 2

Histological Scores of Xenograft Apparatuses
(Mean and raw scores)

| | Cyclosporine A Dose | | | | | | | |
|---|---|---|---|---|---|---|---|---|
| | 0 mg/kg | | 5 mg/kg | | 15 mg/kg | | 30 mg/kg | |
| Tissue Evaluated | Raw Scores | Mean | Raw Scores | Mean | Raw Scores | Mean | Raw Scores | Mean |
| Host reaction | | | | | | | | |
| 3 week | 5.5;6;6 | 5.8 | 5.5;5;5 | 5.2 | 1.5;2;2 | 1.8 | 1.5;2;2 | 1.8 |
| 6 week | 4;5;5 | 4.7 | 5;5;5 | 5.0 | 6;6;6 | 6.0 | 6;6;6 | 6.0 |
| Xenogeneic cells | | | | | | | | |
| 3 week | 2.5;2;2 | 2.2 | 3;3;4 | 3.3 | 5.5;5;5 | 5.2 | 5.5;5;5 | 5.2 |
| 6 week | 1.5;2;1 | 1.5 | 3.5;4;1 | 2.8 | 1.5;2;2 | 1.8 | 2;2;2 | 2.0 |
| Close vascular structures | | | | | | | | |
| 3 week | 3;0;0 | 1.0 | 12;6;2 | 6.7 | 148;123;116 | 129 | 118;104;100 | 107 |
| 6 week | 2;0;1 | 1.0 | 0;0;6 | 2.0 | 0;2;0 | 0.7 | 2;3;4 | 3.0 |

EXAMPLE 3

Survival of Xenogeneic Cells After Cessation of Cyclosporine A Treatment

Xenogeneic cells had poor survival levels when xenografts remained in animals for an additional three weeks after cessation of CSA treatment (Table 2). Such xenografts from Group III and Group IV animals became surrounded by a severe host inflammatory response, and the xenogeneic tissue within the device was destroyed. Few close vascular structures were observed in the vicinity of the implants (Table 2, supra). In addition, the inflammatory response of the host was so strong that host tissue adjacent to the outside of the device was damaged. The increased vascularization observed after 3 weeks of CSA treatment may have been responsible for the vigor of the host immune response. When CSA administration was halted, the vasculature may have allowed rapid influx of host immune system cells. The resulting immune response, in turn, may have caused the disappearance of blood vessels near the xenografts, since none of the Group III or IV xenografts had significantly more close vascular structures than Group I xenografts.

Two of the 3 xenografts from Group II had higher scores for xenogeneic tissue survival compared to xenografts from Group III and Group IV (Table 2). Fibroblasts with patches of epithelial tissue were observed in these 2 xenografts. All 3 xenografts were surrounded by a strong host cellular immune response. However, the size and density of the response was much less than the host response to xenografts from Groups III and IV. None of the xenografts from Group II animals had close vascular structures at 6 weeks, as shown in Table 2 and in FIG. 2 (dark bars). These results indicate that, under these conditions, immunosuppression with CSA for 3 weeks does not continue after CSA administration is halted.

EXAMPLE 4

Effect of a 3 Week Cyclosporine A Treatment on Isogeneic Apparatuses

Isografts from control (Group I) animals had fairly good survival of isogeneic epithelial cells after 3 weeks, but there was limited differentiation of these cells into organized structures. Isografts from animals receiving 5 mg CSA/kg had improved tissue survival and differentiation. Grafts at this dosage of CSA were well vascularized and had a very mild host tissue reaction to the implanted apparatus. Isografts from animals receiving 15 or 30 mg CSA/kg also had excellent tissue survival and very mild host tissue reactions to the implants.

Figure 3:
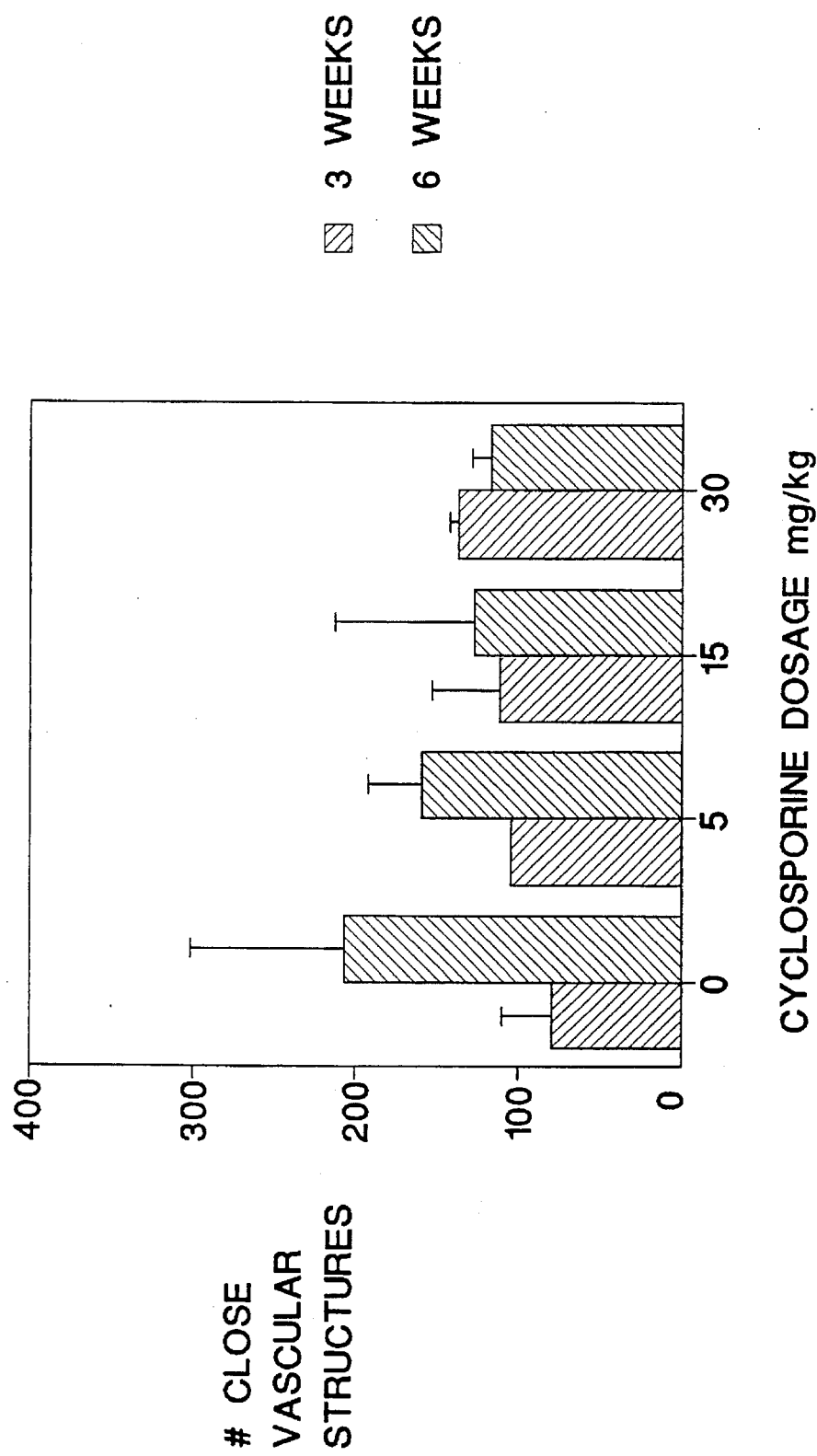
FIG. 3 is a bar graph comparing the mean number of close vascular structures for isografts after daily administration of cyclosporine A for three weeks to the mean number for isografts after daily administration of cyclosporine A for three weeks followed by no cyclosporine A for three weeks.

A gradual increase in close vascular structures with increasing CSA dose was seen with the isografts (FIG. 3, stippled bars). Isografts from animals treated with 30 mg CSA/kg had about sixty percent more close vascular structures than isograft apparatuses from control animals (FIG. 3. stippled bars).

EXAMPLE 5

Survival of Isogeneic Cells After Cessation of Cyclosporine A Treatment

Isografts implanted for 6 weeks survived as well as the isografts implanted for 3 weeks at all dosage levels. The isografts from the control group (Group I) had slightly lower host tissue reaction scores at 6 weeks compared to scores from the control group at 3 weeks. Isografts from Groups II, III and IV had slightly higher host tissue reaction scores at 6 weeks than at 3 weeks. Isografts from all groups had a high number of close vascular structures at 6 weeks, as shown in FIG. 3 (dark bars).

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method for implanting cells in a patient, comprising the steps of:
   (a) providing a population of viable cells;
   (b) implanting into said patient an immunoisolation apparatus having structure defining a cell receiving chamber therein, said immunoisolation apparatus comprising an immunoisolation zone that immunoisolates said cell receiving chamber;
   (c) placing said population into said cell receiving chamber of said immunoisolation apparatus; and
   (d) administering an immunomodulatory agent to said patient in an amount and for a time effective to enhance vascularization of said implanted apparatus.

2. The method of claim 1, wherein said cell population is placed in said cell receiving chamber after said immunoisolation apparatus is implanted in said patient.

3. The method of claim 1 wherein said population of viable cells is capable of producing a therapeutic substance.

4. The method of claim 1, wherein said cell population comprises at least one xenogeneic cell.

5. The method of claim 1, wherein said cell population comprises at least one allogeneic cell.

6. The method of claim 1, wherein said cell population comprises at least one isogeneic cell.

7. The method of claim 3, wherein said cell population comprises at least one cell carrying an extrinsic nucleic acid construct conferring upon said at least one cell the capability of producing said therapeutic substance.

8. The method of claim 1, wherein said immunomodulatory agent is an antiinflammatory agent.

9. The method of claim 1, wherein said immunomodulatory agent is an immunosuppressive agent.

10. The method of claim 1, wherein said immunomodulatory agent is cyclosporine A.

11. The method of claim 1, said immunoisolation apparatus further comprising means for effecting close vascularization of said apparatus.

12. The method of claim 11, wherein said means for effecting close vascularization comprises a vascularization zone.

13. The method of claim 12, wherein said immunoisolation zone is interposed between said vascularizing zone and said cell receiving chamber.

14. The method of claim 11, wherein said means for effecting close vascularization comprises at least one vascularization cell housed within said cell receiving chamber, said vascularization cell producing an effective amount of a vascularizing substance.

* * * * *